United States Patent
Yamakoshi et al.

(10) Patent No.: US 6,395,280 B1
(45) Date of Patent: May 28, 2002

(54) DEODORANT AGENTS FOR ORAL USE FOR DISCHARGES AND METHOD FOR RELIEVING ODOR OF DISCHARGES

(75) Inventors: Jun Yamakoshi, Chba; Shigehiro Kataoka, Chiba; Hiroshi Hosoyama, Chiba; Toshiaki Ariga, Chiba, all of (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 09/601,117

(22) PCT Filed: Mar. 19, 1999

(86) PCT No.: PCT/JP99/01419

§ 371 (c)(1),
(2), (4) Date: Jul. 27, 2000

(87) PCT Pub. No.: WO99/49861

PCT Pub. Date: Oct. 7, 1999

(30) Foreign Application Priority Data

Mar. 31, 1998 (JP) ............................. 10-101720

(51) Int. Cl.[7] ..................... A61K 39/385; A61K 47/00; A61K 35/78
(52) U.S. Cl. ................. 424/195.15; 424/725; 424/76.9; 424/439; 424/766; 424/777
(58) Field of Search .............................. 424/195.1, 401, 424/402, 40, 48–49, 65, 76.5, 76.6, 76.7, 439, 725, 195.15, 766, 777, 76.9; 435/41, 42

(56) References Cited

U.S. PATENT DOCUMENTS 4,311,510 A * 1/1982 Graefe
5,817,299 A * 10/1998 Manirazman
5,906,811 A * 5/1999 Hersh
6,056,971 A * 5/2000 Goldman
6,099,854 A * 8/2000 Howard et al.
6,117,439 A * 9/2000 Kake
6,127,157 A * 10/2000 Hatamoto et al.

FOREIGN PATENT DOCUMENTS

| EP | 0858758 A1 | * | 2/1997 |
| JP | 60-160962 | | 8/1985 |
| JP | 3-200781 | | 9/1991 |
| JP | 4-117326 | | 4/1992 |
| JP | 10-245343 | | 9/1998 |
| JP | 10-161571 | | 10/1998 |
| WO | WO97/45023 | | 12/1997 |

OTHER PUBLICATIONS

"Nishon Kosyueisei Zasshi", *Japanese Journal Of Public Health*, vol. 44, No. 1, 1997, pp. 5–11.

"Utilizing Green Tea Polyphenol to Food", *New Food Industry*, vol. 40, No. 1, 1998, pp. 33–40.

Oszmianski et al., J of Food Science, 50: 1505–6. Changes in grape seed phenols as affected by enzymic and chemical oxidation in vitro, 1985.*

* cited by examiner

*Primary Examiner*—Christopher R. Tate
*Assistant Examiner*—Michele C. Flood
(74) *Attorney, Agent, or Firm*—Young & Thompson

(57) ABSTRACT

An oral deodorant for excreta containing a proanthocyanidin as an active ingredient and a method of reducing the odor of excreta of an object comprising dosing the object with an effective amount of a proanthocyanidin.

1 Claim, 1 Drawing Sheet

DEODORANT AGENTS FOR ORAL USE FOR DISCHARGES AND METHOD FOR RELIEVING ODOR OF DISCHARGES

TECHNICAL FIELD

The present invention relates to an oral deodorant for excreta containing a proanthocyanidin, which is effective on excreta such as excrement and urine and a method of reducing the odor of excrete

BACKGROUND ART

Concern about deodorization of the body odor or the odor of excreta from humans, pets, livestock, etc. has now been growing. For example, the odor of the excreta of domesticated pets such as cats and dogs gives owners discomfort, and the odor of the excreta from a bedridden old, etc. has given rise to a social problem, casting a heavier burden on an attendant.

Under these circumstances, various studies have been conducted on deodorization of the excreta. Proposals include, for example, a method of masking the offensive odor of excreta such as excrement and urine by spraying a fragrance, a method by adsorption of the odor by activated carbon, and a method by scattering a specific compound such as a proanthocyanidin on the source of offensive odors (see Japanese Patent Application Laid-Open No. 60-160962).

All these methods provide measures to be taken against excreted substances, which we can call "post-excretion treatment".

On the other hand, deodorants which are orally taken for the purpose of reducing the bad odor of excreta such as excrement and urine have also been developed. For example, oral deodorants and the like containing, as an active ingredient, mushroom extract (Koizumi Iwao, *Nihon Kosyueisei Zasshi*, vol. 44, No. 1, pp. 5–11 (1997)), green tea extract (Kawakami Masako, *New Food Industry*, Vol. 40, No. 1, pp. 33–40 (1998) or tannic acid (Japanese Patent Application Laid-Open No. 117326/92) are known. However, they are not necessarily satisfactory because of their weak effects or because the practical dose is limited from the economical standpoint.

DISCLOSURE OF THE INVENTION

Accordingly, an object of the present invention is to provide a novel oral deodorant for excreta which is inexpensive and greatly effective and a method of reducing the odor of excreta.

The present inventors have conducted extensive investigations to achieve the above object and surprisingly found as a result that an orally taken proanthocyanidin brings about remarkable reduction in the odor of excreta and that it exhibits quick onset and long duration.

The present invention has been completed based on the above findings and provides an oral deodorant for excreta which contains a proanthocyanidin as an active ingredient.

The present invention also provides an oral deodorant for excreta which contains a proanthocyanidin and mushroom extract as active ingredients.

The present invention further provides a method of reducing the odor of excreta of an object comprising dosing the object with an effective amount of a proanthocyanidin.

The present invention furthermore provides a method of reducing the odor of excreta of an object comprising dosing the object with effective amounts of a proanthocyanidin and mushroom extract.

THE BEST MODE FOR CARRYING OUT THE INVENTION

Figure 1:
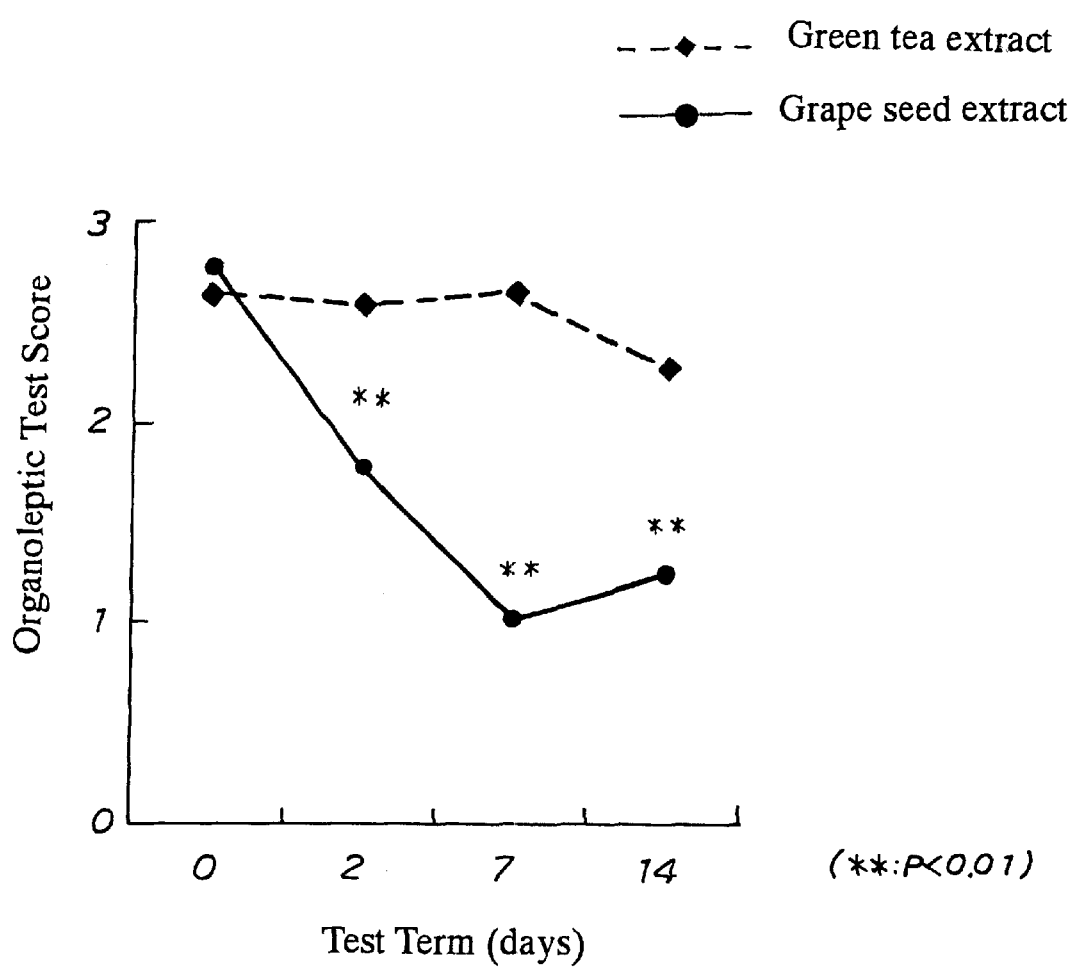
FIG. 1 is graphical representation of the results of the organoleptic test of odor shown in Table 8 of Test Example 5 hereinafter given.

The present invention will be described in the concrete. The oral deodorant for excreta according to the present invention will be described first. Proanthocyanidins are condensed tannin present in various plant parts, i.e., a group of condensation or polymerization compounds comprising, as a constituent unit, flavan-3-ol or flavane-3,4-diol. These compounds release anthocyanidins, such as cyanidin, delphinidin, and pelargonidin, upon being treated with an acid, on which the above naming is based. Proanthocyanidins include procyanidine, prodelphinidin, propelargonidine, and the like which are a dimer, a trimer, a tetramer, or polymers made of ten or more of the above-described units; and stereoisomers thereof. They are obtained by extracting various plant parts, such as grape seeds, grape peel, cranberry fruit, apple fruit, adzuki beans (red beans), bark of sugi trees (Japanese cedar), hinoki trees (Japanese cypress) or pine trees, and the like.

Products comprising proanthocyanidins as a main ingredient are available on the market, including KPA and Gravinol (both available from Kikkoman Corp.; prepared from grape seeds), Applephenon (available from The Nikka Whisky Distilling Co., Ltd.; prepared from immature apple fruit), and Pycnogenol (available from Horphag Research Ltd., Switzerland; prepared from bark of maritime pine trees).

The preparation dose form of the oral deodorant for excreta of the present invention containing a proanthocyanidin as an active ingredient include powders, tablets, capsules, and drinks. The preparation may be supplied in the form of other foods and beverages to which a proanthocyanidin is added. For example, a powdered extract of grape seeds containing a proanthocyanidin may be mixed with appropriate vehicles into tablets or may be mixed with sugar and flavors and made into capsules to provide oral deodorants.

The oral deodorant for excreta according to the present invention can contain known oral deodorant components. In particular, incorporation of mushroom extract is observed to produce a synergistic deodorizing effect.

The mushroom extract is obtained by extracting mushrooms with water or an organic solvent and concentrating and powdering the extract. It is commercially available (e.g., a champignon extract Bio-M, available from Ricom Corp.).

The proanthocyanidin content in the oral deodorant for excreta of the present invention is decided with reference to the dose (effective amount) of the proanthocyanidin hereinafter described, taking the number of doses per day and a daily dose into consideration.

In case where a proanthocyanidin and mushroom extract are used in combination, the compounding ratio and the contents of these ingredients are decided with reference to their administration ratio and doses hereinafter described, taking the number of doses per day and daily doses into consideration.

The method of reducing the odor of excreta according to the present invention will then be described. AL proanthocyanidin is administered by dosing an object with the above-described oral deodorant for excreta, the above-described extract of various plant parts such as grape seeds, or the above-described commercially available product containing a proanthocyanidin as a main component; or by adding the deodorant, extract or commercial product to other foods or beverages to be given to the object.

The dose, i.e., effective amount of the proanthocyanidin is, for instance, 50 mg or more, preferably 60 to 400 mg, in terms of total flavanol (the amount of the proanthocyanidin is calculated in terms of a total flavanol content on (+)-catechin conversion according to the vanillin-HCl method) per day for a person weighing 60 kg. In administering, for example, Gravinol (produced by Kikkoman Corp.) comprising a proanthocyanidin as a main ingredient, which contains about 40% by weight of a proanthocyanidin, to a person weighing 60 kg, it is given at a dose of 125 mg or more, preferably 150 to 1000 mg, in a single or several divided doses a day.

In placing an animal on a proanthocyanidin, the above-described deodorant, extract or commercial product is preferably administered by mixing into the feed in an amount of 0.01 to 1% by weight in terms of total flavanol.

Mushroom extract may be administered in combination with a proanthocyanidin. In this case, where grape seed extract is used as a proanthocyanidin, a preferred administration ratio of the grape seed extract to the mushroom extract is 1:0.05 to 2.0 by weight. For example, the dose of the grape seed extract is 30 mg or more, preferably 50 to 200 mg, in terms of total flavanol per day, and the dose of the mushroom extract is 15 mg or more, preferably 20 to 100 mg, per day for a person weighing 60 kg.

Test Examples are shown below to demonstrate the effects of the present invention.

TEST EXAMPLE 1

Experiment on Rats

Diet used:
(a) MF powder standard diet (available from Oriental Yeast Co., Ltd.)
(b) The MF powder standard diet to which 0.1 wt% of grape seed extract (Gravinol, available from Kikkoman Corp.) was added.
(c) The MF powder standard diet to which 0.5 wt% of mushroom extract (champignon extract (Bio-M) BX100FPD, available from Ricom Corp., containing 21% of powdered extract of mushroom) was added.

A group of animals each consisting of five 6-week-old male Wistar rats were fed on diet (a), (b) or (c), ad lib. The droppings were collected on the 1st, 3rd, and 8th day after the day of administration, and the odor was organoleptically evaluated by 8 panel members on a 0 to 4 scale (odorless: 0; slight odor: 1; medium odor: 2; strong odor: 3). The results are shown in Table 1. The figures indicate the average points.

TABLE 1

|  | Diet (a) Group | Diet (b) Group | Diet (c) Group |
| --- | --- | --- | --- |
| 1st Day | 2.33 ± 0.56 | 1.67 ± 0.88 | 1.75 ± 0.97 |
| 3rd Day | 2.25 ± 0.66 | 1.75 ± 0.66 | 1.89 ± 0.74 |
| 8th Day | 2.25 ± 0.66 | 1.50 ± 0.87 | 1.56 ± 0.83 |

Methyl mercaptan in the headspace of a closed container containing the droppings collected on the 8th day after the administration was measured by gas chromatography. Ammonia and methylamine were determined with a Kitagawa gas detecting tube. The results obtained are shown in Table 2.

TABLE 2

|  | Methyl Mercaptan (ppm) | Ammonia (ppm) | Methylamine (ppm) |
| --- | --- | --- | --- |
| Diet (a) Group | 7.6 ± 1.0 | 26.1 ± 12.4 | 11.4 ± 7.8 |
| Diet (b) Group | 1.6 ± 2.1** | 1.9 ± 3.1* | 3.9 ± 2.3 |
| Diet (c) Group | 1.7 ± 1.5** | 2.6 ± 1.2* | 4.5 ± 2.9 |

Note
*Significant at the level of 5%
**Significant at the level of 1%

As is apparent from the results in Tables 1 and 2, the odor of the group fed on the grape seed extract added diet ((b) group) was weak from the first day after the administration, proving the deodorizing effect stronger than as observed in the group fed on the mushroom extract-added diet ((c) group). The substances giving off bad odors (methyl mercaptan, ammonia and methylamine) of the droppings of the (b) group on the 8th day after the administration were less than those of the group (c).

TEST EXAMPLE 2

Combination of Grape Seed Extract and Mushroom Extract

Diet used:
(a) MF powder standard diet
(b) The MF powder standard diet to which 0.1 wt% of grape seed extract (Gravinol, available from Kikkoman Corp.) was added.
(c) The MF powder standard diet to which 0.05 wt% of grape seed extract (Gravinol, available from Kilioman Corp.) and 0.25 wt% of the same mushroom extract as used in Test Example 1 were added.

A group of animals each consisting of five 15-week-old female SD rats were fed on diet (a), (b) or (c), ad lib. The droppings were collected on the 1st, 3rd, and 8th day after the administration, and the odor was organoleptically evaluated in the same manner as in Test Example 1. The results are shown in Table 3.

TABLE 3

|  | Diet (a) Group | Diet (b) Group | Diet (c) Group |
| --- | --- | --- | --- |
| 1st Day | 2.32 ± 0.56 | 1.52 ± 0.96 | 1.14 ± 0.71* |
| 3rd Day | 2.42 ± 0.57 | 1.67 ± 0.55 | 1.21 ± 0.76* |
| 8th Day | 2.19 ± 0.59 | 1.48 ± 0.50 | 1.14 ± 0.64* |

Note:
*Significant at the level of 5%

Ammnonia and methylamine of the droppings on the 8th day after the administration were determined in the same manner as in Test Example 1. The results are shown in Table 4.

TABLE 4

|  | Ammonia (ppm) | Methylamine (ppm) |
| --- | --- | --- |
| Diet (a) Group | 9.3 ± 5.3 | 12.0 ± 7.1 |
| Diet (b) Group | 7.6 ± 2.1 | 6.3 ± 1.3 |
| Diet (c) Group | 3.3 ± 2.1* | 4.3 ± 2.9 |

*Significant at the level of 5%

As is apparent from the results in Tables 3 and 4, the (c) group fed on the combination of the grape seed extract and the mushroom extract showed markedly high deodorizing effects.

TEST EXAMPLE 3

Experiment on Pigs

Diet used:

(a) Standard diet for pigs (b) The standard diet for pigs to which 0.375 wt% of grape seed extract (KPA-40, available from Kikkoman Corp.) was added.

(c) The standard diet for pigs to which 0.075 wt% of grape seed extract (KPA-40, available from Kikkoman Corp.) was added.

Twelve piglets (four per group) were fed on each of the diets (a), (b) and (c) for 3 weeks ad lib. The droppings were then collected, and the odor was organoleptically evaluated in the same manner as in Test Example 1. The results are shown in Table 5.

TABLE 5

| | Diet (a) Group | Diet (b) Group | Diet (c) Group |
|---|---|---|---|
| After 3 Weeks of Administration | 2.7 ± 0.7 | 1.8 ± 0.8 | 2.2 ± 0.4 |

As a result, dose-dependent deodorizing effects were observed.

TEST EXAMPLE 4

On Humans

Male adults aging between 35 and 45 were grouped into two each consisting of three. Groups (a) and (b) were asked to take 250 mg of grape seed extract (Gravinol, available from Kikkoman Corp.) or the same mushroom extract as used in Test Example 1, respectively, in the morning and the evening (total dose: 500 mg) for 4 days and to organoleptically evaluate the odor of their own excrement in the same manner as in Test Example 1. Further, after they stopped taking, the same evaluation was made on their excrement for 3 days (on the 4th, 5th and 6th days). Further, a sample was taken of the excrement of one person of each of the groups (a) and (b) everyday, and the substances causing bad odors were measured in the same manner as in Test Example 1. The results obtained are shown in Tables 6 and 7.

TABLE 6

| | Group (a) | Group (b) |
|---|---|---|
| The Preceding Day | 2.67 ± 0.47 | 2.67 ± 0.47 |
| The Day of Taking | 2.33 ± 0.47 | 2.67 ± 0.47 |
| 1st Day | 1.0 ± 0* | 2.33 ± 0.47 |
| 2nd Day | 1.0 ± 0* | 1.67 ± 0.47 |
| 3rd Day | 1.0 ± 0* | 1.0 ± 0* |
| 4th Day | 1.0 ± 0* | 1.0 ± 0* |
| 5th Day | 1.0 ± 0* | 2.67 ± 0.47 |
| 6th Day | 2.67 ± 0.47 | 2.67 ± 0.47 |

Note:
*Significant at the level of 5%

TABLE 7

| | Methyl Mercaptan (ppm) | | Ammonia (ppm) | | Methylamine (ppm) | |
|---|---|---|---|---|---|---|
| | Group (a) | Group (b) | Group (a) | Group (b) | Group (a) | Group (b) |
| The Preceding Day | 10 | 7.5 | 0 | 0.3 | 1 | 1.5 |
| The Day of Taking | 10 | 10 | 1 | 0.5 | 1 | 2 |
| 1st Day | 2 | 11 | 0 | 0.5 | 0 | 1 |
| 2nd Day | 2 | 7.5 | 0 | 0.5 | 0 | 1 |
| 3rd Day | 2.4 | 4.5 | 0 | 0.5 | 0 | 1 |
| 4th Day | 2 | 2 | 0 | 0.1 | 0 | 4 |
| 5th Day | 3 | 7.5 | 0 | 0.1 | 0 | 2.7 |
| 6th Day | 9 | 10 | 0 | 0 | 0 | 1 |

It was confirmed from Tables 6 and 7 that the group (a) placed on the grape seed extract exhibited very powerful deodorizing effects on the excrement from the next day of internal taking and that the effects persisted for 2 days after the internal taking was stopped.

TEST EXAMPLE 5

Experiment on Humans

Male adults aging between 35 and 45 were grouped into two each consisting of nine persons and asked to take 250 mg of grape seed extract (Gravinol, available from Kikkoman Corp.; containing 200 mg of flavanol per 500 mg) (group (a)) or green tea extract (Sunflavon HG, available from Taiyo Kagaku K.K.; containing 250 mg of flavanol per 500 mg) (group (b)) in the morning and the evening (total dose: 500 mg) for 14 days and to organoleptically evaluate the odor of their excrement on the day before the taking and the 2nd, 7th and 14th day from the day of the taking in the same manner as in Test Example 1. Further, the excrement samples on the preceding day and the 14th day were subjected to measurement of the number of bifid bacterial cells and the amount of intestinal decomposition products (e.g., phenol, p-cresol, 4E-phenol, indole, and skatole). The results are shown in Table 8 and FIG. 1.

The test subjects were instructed not to take antibiotics, teas (e.g., green tea and oolong tea), fermented milk products (e.g., yogurt), oligosaccharide-added foods, dietary fiber-enriched foods, fermented soybeans, polyphenol-containing foods, and red wine during the testing time.

TABLE 8

| | Group (a) | Group (b) |
|---|---|---|
| The Preceding Day | 2.76 ± 0.44 | 2.63 ± 0.50 |
| 2nd Day | 1.77 ± 0.64** | 2.58 ± 0.50 |
| 7th Day | 1.0 ± 0** | 2.63 ± 0.58 |
| 14th Day | 1.24 ± 0.44** | 2.26 ± 0.65 |

Note:
**Significant at the level of 1%

The number of bifid bacterial cells (logCFU/g-excrement), which was 9.6±0.3 on the preceding day of taking, increased significantly to 10.1±0.3 (significant at the level of 5%) on the 14th day of taking the grape seed extract. In group (a) taking the grape seed extract, the measurement of intestinal decomposition products ($\mu$g/g) revealed that phenol, which was 10.1±17.1 on the preceding day, decreased to 0.5±0.5 on the 14th day. Similarly, p-cresol decreased from 31.7±28.9 to 16.4±8.5, 4E-phenol decreased from 0.2±0.5 to 0, indole decreased from 19.5±8.3 to 14.2±5.0, and skatole decreased from 2.5±3.7 to 0.6±1.2. The total amount of these decomposition products was 63.9±25.0 on the preceding day, while it significantly decreased to 31.8±12.5 (significant at the level of 5%) on the 14th day of taking. From these observations, it is considered that the deodorizing effect of the grape seed extract is attributed to reduction of intestinal decomposition products by increase of bifid bacteria.

Examples are shown hereunder.

EXAMPLE 1

| | |
|---|---|
| Grape seed extract (Gravinol, available from Kikkoman Corp.) | 10 wt % |
| Lactose | 80 wt % |
| Magnesium stearate | 10 wt % |

The above components were mixed and tableted in a usual manner to produce oral deodorant tablets for excreta each weighing 300 mg.

EXAMPLE 2

In the production of dry cat food, 0.05% of grape seed extract (KPA-40, available from Kikkoman Corp.) was added to prepare a pet food containing an oral deodorant for excreta.

EXAMPLE 3

Grape seed extract (Gravinol, available from Kikkoman Corp.) and mushroom extract (champignon extract (Bio-M) BX100FPD, available from Ricom Corp.) were mixed at a ratio of 2:1. The mixture was compounded as follows and tableted in the same manner as in Example 1 to obtain an oral deodorant.

| | |
|---|---|
| Mixture of grape seed extract and mushroom extract | 50 wt % |
| Lactose | 45 wt % |
| Magnesium stearate | 5 wt % |

Industrial Applicability

When taken internally, the oral deodorant for excreta according to the present invention remarkably reduces the odor of excreta of the taker. It is so rapid in acting as to manifest its effect on the next day of the internal taking. It is effective in deodorizing the excreta of not only humans but livestock and pets, etc., being mixed into their diets.

Further, the method of reducing the odor of excreta according to the present invention reduces the odor of the excreta of humans or animals sufficiently, inexpensively, and easily.

What is claimed:

1. A method of reducing the odor of excreta of a subject wherein the subject performs the step of orally ingesting effective amounts of a mushroom extract and effective amounts of proanthocyanidin-containing grape seed extract or a proanthocyanidin-containing grape peel extract.

* * * * *